United States Patent
Karlsson

(10) Patent No.: US 11,022,609 B2
(45) Date of Patent: Jun. 1, 2021

(54) METHOD FOR DETERMINING INTERACTION KINETICS WITH RAPID DISSOCIATION

(71) Applicant: GE Healthcare Bio-Sciences AB, Uppsala (SE)

(72) Inventor: Olof Karlsson, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 285 days.

(21) Appl. No.: 15/034,084

(22) PCT Filed: Nov. 12, 2014

(86) PCT No.: PCT/EP2014/074396
§ 371 (c)(1),
(2) Date: May 3, 2016

(87) PCT Pub. No.: WO2015/074931
PCT Pub. Date: May 28, 2015

(65) Prior Publication Data
US 2016/0282342 A1    Sep. 29, 2016

Related U.S. Application Data

(60) Provisional application No. 61/905,962, filed on Nov. 19, 2013.

(51) Int. Cl.
| | | |
|---|---|---|
| *G01N 33/48* | (2006.01) | |
| *G01N 33/543* | (2006.01) | |
| *G01N 21/27* | (2006.01) | |
| *G01N 21/552* | (2014.01) | |
| *G06G 7/58* | (2006.01) | |

(52) U.S. Cl.
CPC ..... *G01N 33/54373* (2013.01); *G01N 21/272* (2013.01); *G01N 21/553* (2013.01); *G01N 21/554* (2013.01)

(58) Field of Classification Search
None
See application file for complete search history.

(56) References Cited

U.S. PATENT DOCUMENTS

| | | |
|---|---|---|
| 5,242,828 A | 9/1993 | Bergstrom et al. |
| 5,313,264 A | 5/1994 | Ivarsson et al. |
| 5,436,161 A | 7/1995 | Bergstrom et al. |
| 5,492,840 A | 2/1996 | Malmqvist et al. |
| 5,573,956 A | 11/1996 | Hanning |
| 5,641,640 A | 6/1997 | Hanning |
| 2005/0131650 A1 | 6/2005 | Andersson et al. |
| 2013/0196343 A1 | 8/2013 | Mastrangelo et al. |

FOREIGN PATENT DOCUMENTS

| | | |
|---|---|---|
| JP | 2006-098370 A | 4/2006 |
| WO | 2005/029077 A1 | 3/2005 |
| WO | 2005029077 A1 | 3/2005 |
| WO | 2011/065913 A1 | 6/2011 |

OTHER PUBLICATIONS

International Search Report and Written Opinion regarding International Application No. PCT/EP2014/074396, dated Feb. 2, 2015, 13 pages.
Stenlund et al., "Studies of small molecule interactions with protein phosphates using biosensor technology", Analytical Biochemistry, Academic Press Inc., New York, vol. 353, No. 2, Mar. 20, 2006, pp. 217-225.
Machine Translation and Notification of reasons for refusal issued in connection with corresponding JP Application No. 2016-553727 dated Aug. 28, 2018.
Chinese Patent Office, "Decision on Rejection," issued in connection with Chinese patent application No. 2014800630979, dated Jun. 2, 2020, 5 pages.

*Primary Examiner* — Eric S Dejong
(74) *Attorney, Agent, or Firm* — Hanley, Flight & Zimmerman, LLC

(57) ABSTRACT

The invention relates to a method for determining interaction kinetics for an analyte. The method comprises first contacting a solution containing the analyte with immobilized ligand, or analogue thereof, immobilized on an optical sensor surface; monitoring the binding of the analyte to the immobilized ligand or analogue, wherein the binding is measured as a resulting change in a property of the surface; and automatically determining the interaction kinetics, which determining step includes first defining parts of the dissociation phase that contains kinetic information for fitting. The invention further relates to an analytical system for studying molecular interactions, which system is capable of performing the novel method, as well as a computer program product for performing the steps of the method.

11 Claims, 2 Drawing Sheets

METHOD FOR DETERMINING INTERACTION KINETICS WITH RAPID DISSOCIATION

CROSS-REFERENCE TO RELATED APPLICATIONS

This application is a filing under 35 U.S.C. 371 of international application number PCT/EP2014/074396, filed Nov. 12, 2014, which claims priority to U.S. application No. 61/905,962, filed Nov. 19, 2013, the entire disclosures of each of which are hereby incorporated by reference.

FIELD OF THE INVENTION

The present invention relates to a method for determining interaction kinetics for an analyte. More specifically, the invention relates to a method for automatically determining interaction kinetics, which includes first defining parts of the dissociation phase that contains kinetic information. The invention also relates to an analytical system and a computer program product for performing steps of the method.

BACKGROUND OF THE INVENTION

A variety of analytical techniques are used to characterize interactions between molecules, particularly in the context of assays directed to the detection and interaction of biomolecules. For example, antibody-antigen interactions are of fundamental importance in many fields, including biology, immunology and pharmacology. In this context, many analytical techniques involve binding of a "ligand", such as an antibody, to a solid support, followed by contacting the ligand with an "analyte", such as an antigen. Following contact of the ligand and analyte, some characteristic is measured which is indicative of the interaction, such as the ability of the ligand to bind the analyte. It is often desired that after measurement of the interaction, it should be possible to dissociate the ligand-analyte pair in order to "regenerate" free ligand, thereby enabling reuse of the ligand surface for a further analytical measurement.

Analytical sensor systems that can monitor such molecular interactions in real time are gaining increasing interest. These systems are often based on optical biosensors and usually referred to as interaction analysis sensors or biospecific interaction analysis sensors. A representative biosensor system is the Biacore® instrumentation sold by GE Healthcare Life Sciences, which uses surface plasmon resonance (SPR) for detecting interactions between molecules in a sample and molecular structures immobilized on a sensing surface. With the Biacore® systems it is possible to determine in real time without the use of labeling not only the presence and concentration of a particular molecule in a sample, but also additional interaction parameters such as, for instance, the association rate and dissociation rate constants for the molecular interaction. The apparatus and theoretical background are fully described in the literature (see eg Jonsson, U., et al., BioTechniques 11: 620-627 (1991)). Essentially, the technique involves the immobilization of a ligand to the special surface of a sensor chip, contacting the sensor chip with a flow of sample containing the analyte of interest, and then measuring the change in the surface optical characteristics of the sensor chip arising from the binding of interest. For further details on SPR, reference is also made to U.S. Pat. Nos. 5,313,264, 5,573,956 and 5,641,640.

Frequently in SPR analysis, data sets for kinetics are produced where the dissociation data collection time is excessive in relation to the dissociation of the interactants (i.e., ligands and analytes). The excessive data does not contain any kinetic information but could disturb the fitting process so that the kinetic rate constants cannot be determined or are less accurate. This failure can in many cases be avoided if the fitting is limited to the information containing part of the sensorgrams. This is easily done in the BIAeval software of the Biacore® systems where the fitting range is set manually by the operator for each data set. A manual process is however incompatible with the desire for conducting fully automated kinetic evaluation.

There is a need, therefore, to implement an automated process for identifying and removing excessive data, thus enabling fully automatic kinetic evaluation of the interaction between ligands and analytes.

BRIEF SUMMARY OF THE INVENTION

Disclosed herein are novel methods for complementing the fitting process using an algorithm that automatically excludes the excessive data from the fitting. The method and algorithm automatically excludes from the fitting process the part of the dissociation phase that follows complete dissociation back to baseline. This method increases the success rate for fitting of rapid interaction kinetics and further facilitates big kinetic runs with many data sets.

Thus, a first aspect of the present invention is to provide a method for determining interaction kinetics of an analyte with a binding agent immobilized to a solid support surface by contacting the surface with a fluid sample containing the analyte, monitoring the binding of the analyte to the immobilized ligand or analogue, wherein the binding is measured as a resulting change in a property of the surface; and automatically determining the interaction kinetics, which determining step includes first defining parts of the dissociation phase that contains kinetic information for fitting. In certain embodiments, the determining step further includes adjusting for drifts, disturbances or single deviating curves.

In certain embodiments, the ligand, or analogue thereto, is immobilized to a series of surfaces, and the analyte is contacted with each of the surfaces in parallel.

In certain embodiments, the analyte is provided in a concentration series, and interaction kinetics is calculated from interaction between the series of analytes and the surface immobilized ligand or analogue.

In certain embodiments, the optical sensor surface is part of a detector based upon evanescent wave sensing. Preferably, the optical sensor surface is part of a detector based upon surface plasmon resonance.

In certain embodiments, the method of defining parts of the dissociation phase that contains kinetic information for fitting is done by excluding response data less than:

$$R = Y_{high}/x$$

wherein R is the response in RU below which the algorithm excludes dissociation phase data from fitting $Y_{high}$ is the highest response relative to baseline during the dissociation phase on each curve x is an arbitrary number set by user or coded in the program software.

In other embodiments, the method of defining parts of the dissociation phase that contains kinetic information for fitting is done by excluding response data less than R=0 (baseline).

In still other embodiments, the method of defining parts of the dissociation phase that contains kinetic information for fitting is done by excluding response data less than R=x (x is a number set by user or coded in the program).

In another aspect, the present invention provides an analytical system for studying molecular interactions, which comprises computer processing means including program code means for performing the steps of the methods.

In still another aspect, the present invention provides a computer program product comprising program code means stored on a computer readable medium or carried on an electrical or optical signal for performing the steps of the methods.

Further details and advantages of the present invention will appear from the description and claims below.

DETAILED DESCRIPTION OF THE INVENTION

Figure 1A:
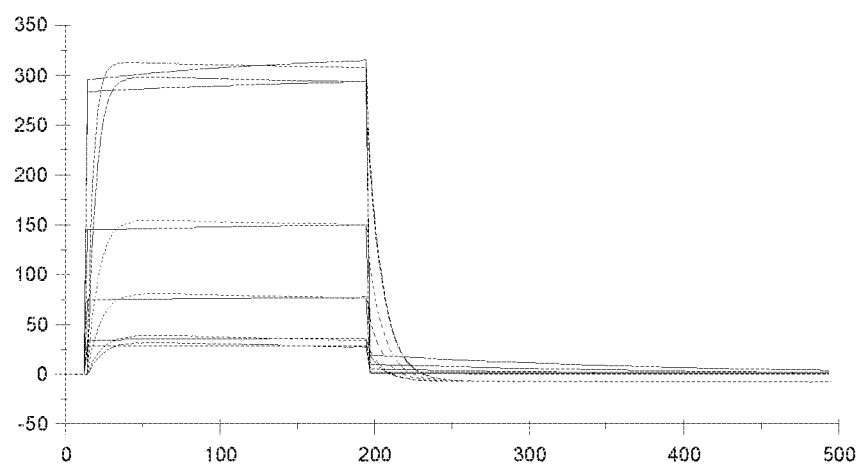
FIG. 1 (a) Upper panel: A data set is fitted with the 1:1-binding model using the entire dissociation phase set in the run method. (b) Lower panel: The fitting is repeated with only the relevant part of the dissociation phase included.

The invention relates to novel methods for determining interaction kinetics for an analyte, as well as an analytical system and a computer program product for performing steps of the method. Thus, in one aspect, the present invention relates to a method for determining interaction kinetics for an analyte, comprising:
 (a) contacting a solution containing the analyte with immobilized ligand, or analogue thereof, immobilized on an optical sensor surface;
 (b) monitoring the binding of the analyte in the solution to the immobilized ligand or analogue, wherein the binding is measured as a resulting change in a property of the surface; and
 (c) automatically determining the interaction kinetics, which determining step includes first defining parts of the dissociation phase that contains kinetic information for fitting.

Surface binding interactions may be characterized using a number of different interaction analysis techniques. Commercially available biosensors include the above-mentioned Biacore® system instruments, which are based on surface plasmon resonance (SPR) and permit monitoring of surface interactions in real time.

The phenomenon of SPR is well known. SPR arises when light is reflected under certain conditions at the interface between two media of different refractive indices, and the interface is coated by a metal film, typically silver or gold. In the Biacore® instruments, the media are the sample and the glass of a sensor chip that is contacted with the sample by a microfluidic flow system. The metal film is a thin layer of gold on the chip surface. SPR causes a reduction in the intensity of the reflected light at a specific angle of reflection. This angle of minimum reflected light intensity varies with the refractive index close to the surface on the side opposite from the reflected light, in the Biacore® system the sample side.

When molecules in the sample bind to the capturing molecules on the sensor chip surface, the concentration, and therefore the refractive index at the surface changes and an SPR response is detected. Plotting the response against time during the course of an interaction will provide a quantitative measure of the progress of the interaction. Such a plot is usually called a sensorgram. In the Biacore® system, the SPR response values are expressed in resonance units (RU). One RU represents a change of 0.00001° in the angle of minimum reflected light intensity, which for most proteins is roughly equivalent to a change in concentration of about 1 pg/mm$^2$ on the sensor surface. As sample containing an analyte contacts the sensor surface, the capturing molecule (ligand) bound to the sensor surface interacts with the analyte in a step referred to as "association." This step is indicated on the sensorgram by an increase in RU as the sample is initially brought into contact with the sensor surface. Conversely, "dissociation" normally occurs when sample flow is replaced by, for example, a buffer flow. This step is indicated on the sensorgram by a drop in RU over time as analyte dissociates from the surface-bound ligand.

A representative set of sensorgrams (binding curves) for reversible interactions of six different analyte concentrations at the sensor chip surface is presented in FIG. 1, the sensing surface having an immobilized molecule (ligand), for example an antibody, interacting with analyte in a sample. The vertical axis (y-axis) indicates the response (here in resonance units, RU) and the horizontal axis (x-axis) indicates the time (here in seconds, s). Initially, buffer is passed over the sensing surface giving the baseline response in the sensorgram. During sample injection, an increase in signal is observed due to binding of the analyte. This part of the binding curve is usually referred to as the "association phase". Eventually, a steady state condition is reached where the resonance signal plateaus. At the end of sample injection, the sample is replaced with a continuous flow of buffer and a decrease in signal reflects the dissociation, or release, of analyte from the surface. This part of the binding curve is usually referred to as the "dissociation phase". The shape of the association/dissociation curve provides valuable information regarding the interaction kinetics, and the height of the resonance signal represents surface concentration (i.e., the response resulting from an interaction is related to the change in mass concentration on the surface).

There are a number of useful models for kinetic evaluation. The simplest is the 1:1 binding model. Other models include, for example, 1:1 dissociation model, the bivalent analyte model, the heterogeneous analyte model, the heterogeneous ligand model, the two state reaction model and the 1:1 model with mass transfer. See, e.g., Biacore T200 Software Handbook 28-9768-78 Edition AA. The embodiments of the invention are suited for all the kinetic models.

For a 1:1 binding model, assuming a reversible reaction (which is not mass transfer limited) between an analyte A and a surface-bound (immobilized) capturing molecule B (first order kinetics):

$$A+B \Leftrightarrow AB$$

The rate of change in surface concentration of A during analyte injection is $$\frac{d\Gamma}{dt} = k_{ass}(\Gamma_{max} - \Gamma)C - k_{diss}\Gamma$$

where $\Gamma$ is the concentration of bound analyte, $\Gamma_{max}$ is the maximum binding capacity of the surface, $k_{ass}$ is the association rate constant, $k_{diss}$ is the dissociation rate constant, and C is the bulk analyte concentration. Rearrangement of the equation gives:

$$\frac{d\Gamma}{dt} = k_{ass}C\Gamma_{max} - (k_{ass}C + k_{diss})\Gamma$$

If all concentrations are measured in the same units, the equation may be rewritten as:

$$\frac{dR}{dt} = k_{ass}CR_{max} - (k_{ass}C + k_{diss})R$$

where R is the response in RU. In integrated form, the equation is:

$$R = \frac{k_{ass}CR_{max}}{k_{ass}C + k_{diss}}(1 - e^{-(k_{ass}C + k_{diss})t})$$

The rate of dissociation can be expressed as:

$$\frac{dR}{dt} = -k_{diss}R$$

and in integrated form:

$$R = R_0 \cdot e^{-k_{diss}t}$$

Affinity is expressed by the equilibrium association constant $K_A = k_{ass}/k_{diss}$ or the equilibrium dissociation constant $K_D = k_{diss}/k_{ass}$.

For a 1:1 binding model with mass transfer (which is used in newer version software), curve fitting of the entire inhibitor concentration series data set (global fit) may be performed using numerical calculations of the equation system:

$A[0]=0$ $dA/dt=kt*(\text{Conc}-A)-(ka*A*B-kd*AB)$ where A is the concentration of analyte at the sensor surface,
B is the immobilized interactant and
Conc is the injected analyte concentration $[0]=R \text{ max}$ $dB/dt=-(ka*A*B-kd*AB)$ $AB[0]=0$ $dAB/dt=(ka*A*B-kd*AB)$ Total response:

$AB+RI$ where RI is the refractive index mismatch between the sample and the running buffer.

For a more detailed description of the determination of molecular interaction kinetics, it may be referred to, for example, Karlsson, R. and Fält, A. (1997) Journal of Immunological Methods, 200, 121-133. See also Nordin et al., (2005) Analytical Biochemistry, 340, 359-368.

Once the rate equations are generated, the values for parameters in the rate equation that best fit the experimental data need to be determined. This is generally referred to as curve fitting. One method used for curve fitting relies on the Marquardt-Levenberg algorithm, which optimizes parameter values by minimizing the sum of the squared residuals. The residuals are the difference between the calculated and experimental curves at each point: squared residuals are used so that deviations above and below the experimental curve are weighted equally:

$$S = \sum_{1}^{n}(r_f - r_x)^2$$

where S is the sum of squared residuals
$r_f$ is the fitted value at a given point
$r_x$ is the experimental value at the same point
and n is the number of data points The closeness of the fit is described by the statistical value of chi-square:

$$x^2 = \frac{\sum_{1}^{n}(r_f - r_x)^2}{n - p}$$

where $r_f$ is the fitted value at a given point
$r_x$ is the experimental value at the same point
n is the number of data points
and p is the number of fitted parameters For sensorgram data, the number of data points is very much larger than the number of fitted parameters in the model, so $n - p \approx n$ and chi-square reduces to the average squared residual per data point.

If the model fits the experimental data precisely, chi-square represents the mean square of the signal noise (since this is the only deviation from the fitted curve).

Figure 1B:
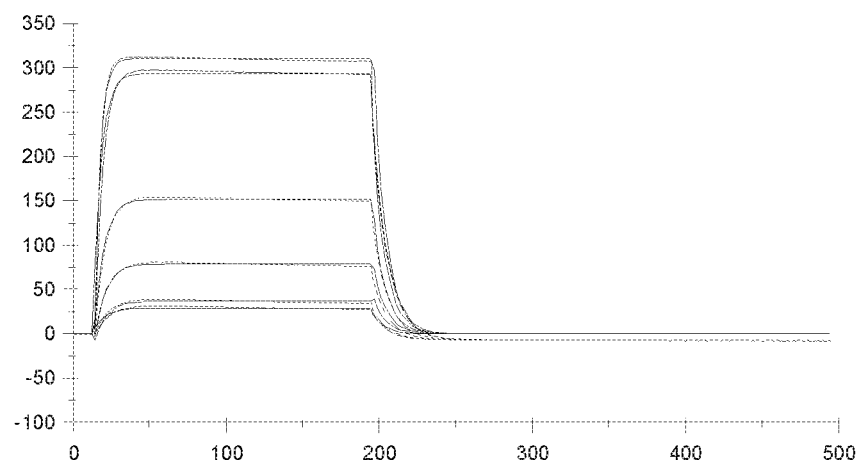

As discussed above, when running kinetics with one or several interacting pairs with unknown interaction kinetics in the same run, contact time and dissociation time need to be set to suit the expected slowest interactants and these times are kept similar throughout the run. For data sets with rapid dissociation this means that after complete dissociation, data is still being recorded as dissociation data when the response has gone back to baseline (FIG. 1a). When fitting the 1:1 interaction model to such data set the entire dissociation phase is generally used for fitting meaning that the non-kinetic part will have as much influence on the fitting as the kinetic part. This occasionally causes the algorithm to find a $chi^2$ minimum without fitting to the kinetic shape of the curves, i.e., kinetic determination fails (FIG. 1a, compare the coloured data curves with the black fitted curves). However, when the part of the dissociation that is used for fitting is manually limited to the kinetic part (240 seconds in this instance) the algorithm finds the shape of the curves (FIG. 1b, compare the coloured data curves with the black fitted curves). The kinetic rate constants are now determined. This is due to the fact that irrelevant and disturbed data do not dominate the $chi^2$ calculation.

In one embodiment, an algorithm is added to define parts of the dissociation phase that contains kinetic information.

Figure 2A:
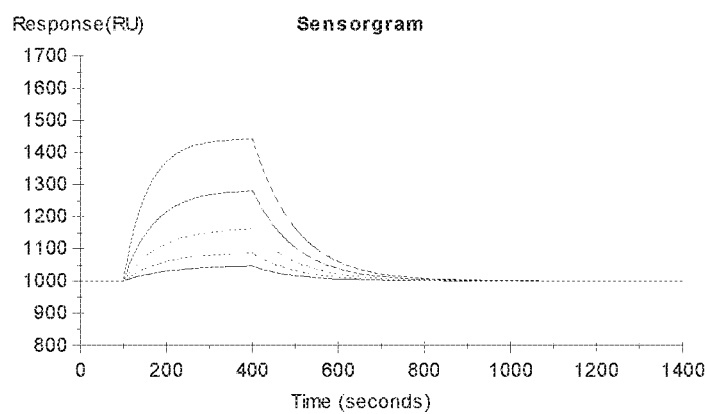
FIG. 2 (a) Upper panel: a complete dataset collected over 1400 seconds; (b) Middle panel: shows the dataset of (a) but limited to the part used for fitting when an algorithm is applied; (c) Lower panel: a dataset with slow dissociation over 1400 seconds.

For a data set shown in FIG. 2(a), the standard algorithm for fitting would use the entire dissociation phase for fitting (e.g., 400-1400 s). In one implementation of the current invention, the part used for fitting is delimited by the following algorithm:

$$R=Y_{high}/x$$

where R is the response in RU below which the algorithm excludes dissociation phase data from fitting $Y_{high}$ is the highest response relative to baseline during the dissociation phase on each curve x may be an arbitrary number set by user or coded in the program software. Thus, when x=20, the data with an R less than 5% of the highest response will be excluded during fitting. Care should be taken in setting the appropriate number x. When the number is too high, the result could be affected if there are drifts in the curve; when the number is too low, useful data may be inadvertently excluded.

Figure 2B:
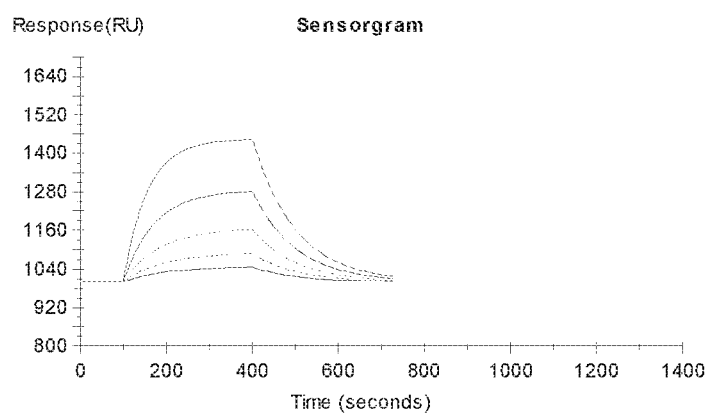
Figure 2C:
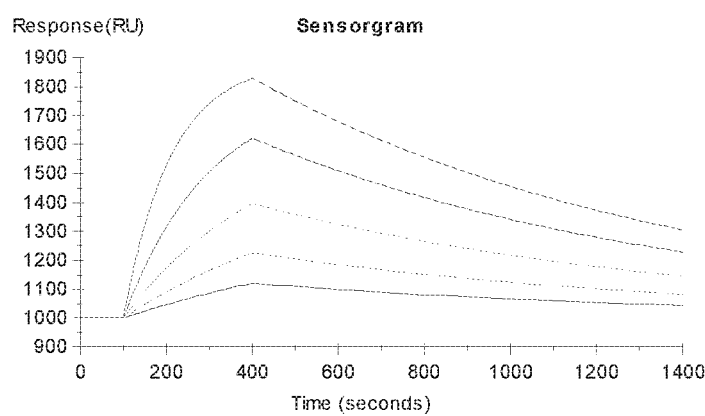

For each curve in the dataset, only the information containing part as determined by the algorithm is used for fitting (FIG. 2(b), assuming x=20). The algorithm does not affect datasets with slow dissociation, which is beneficial (FIG. 2(c)).

In another implementation, the part used for fitting is delimited by a simpler algorithm such as R=0 (baseline) or R=x (an arbitrary number set by user or coded in the program). None of these simpler algorithms affect datasets with slow dissociation, which is beneficial, but they could be less efficient with noisy or drifting data.

Optionally, in certain applications, drifts, disturbances and single deviating curves etc. will also be taken into account.

The method streamlines and makes kinetic evaluation of kinetic data simpler and enhances kinetic evaluation of big runs containing many kinetic data sets.

In a variation of the current embodiments, similar algorithms could be implemented to have the control software stop generating data when dissociation is complete. Alternatively, similar algorithms could be implemented to have the evaluation software to cut away the disturbing part of the data.

While the description above has been made with some respect to the Biacore® systems, it is understood that the invention may be used in connection with numerous other techniques for detecting binding interactions at the solid support surface, including, e.g., those relying on a label, such as a radiolabel, a chromophore, a fluorophore, a marker for scattering light, an electrochemically active marker (e.g., field effect transistor based potentiometry), an electric field active marker (electro-stimulated emission), a magnetically active marker, a thermoactive marker, a chemiluminescent moiety or a transition metal, as well as so-called label free detection systems. Real time detection systems are, however, preferred, especially those based on chemical sensor or biosensor technology.

A biosensor is broadly defined as a device that uses a component for molecular recognition (for example a layer with immobilized antibodies) in either direct conjunction with a solid state physicochemical transducer, or with a mobile carrier bead/particle being in conjunction with the transducer. While such sensors are typically based on label free techniques, detecting, e.g., a change in mass, refractive index, or thickness for the immobilized layer, there are also sensors relying on some kind of labelling. Typical sensor detection techniques include, but are not limited to, mass detection methods, such as optical, thermo-optical and piezoelectric or acoustic wave (including, e.g., surface acoustic wave (SAW) and quartz crystal microbalance (QCM)) methods, and electrochemical methods, such as potentiometric, conductometric, amperometric and capacitance/impedance methods. With regard to optical detection methods, representative methods include those that detect mass surface concentration, such as reflection-optical methods, including both external and internal reflection methods, which may be angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, critical angle refractometry, frustrated total reflection (FTR), scattered total internal reflection (STIR) which may include scatter enhancing labels, optical wave guide sensors; external reflection imaging, evanescent wave-based imaging such as critical angle resolved imaging, Brewster angle resolved imaging, SPR angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers, waveguide leaky mode spectroscopy, reflective interference spectroscopy (RIfS), transmission interferometry, holographic spectroscopy, and atomic force microscopy (AFR).

Commercially available today are inter alia bio sensor systems based on SPR. Exemplary such SPR-biosensors include the above-mentioned Biacore® instruments. A detailed discussion of the technical aspects of the Biacore® instruments and the phenomenon of SPR may be found in U.S. Pat. No. 5,313,264. More detailed information on matrix coatings for biosensor sensing surfaces is given in, for example, U.S. Pat. Nos. 5,242,828 and 5,436,161. In addition, a detailed discussion of the technical aspects of the biosensor chips used in connection with the Biacore® instruments may be found in U.S. Pat. No. 5,492,840. The full disclosures of the above-mentioned U.S. patents are incorporated by reference herein.

It may many times be convenient to carry out the method of the invention in a flow cell, e.g., of the type used in the above-mentioned Biacore® instruments. Other flow cells that may be used in the present invention are also well known to the skilled person and need not be described herein.

It is to be noted that the term "solid support" as used herein is to be interpreted broadly and is meant to comprise any solid (flexible or rigid) substrate onto which one or more binding agents can be immobilized and molecular interactions therewith be detected by the particular detection system chosen. The substrate may be biological, non-biological, organic, inorganic or a combination thereof, and may be in the form of particles, strands, precipitates, gels, sheets, tubings, spheres, containers, capillaries, pads, slices, films, plates, slides, etc, having any convenient shape, including disc, sphere, circle, etc. The substrate surface may have any two-dimensional configuration and may include, for example steps, ridges, kinks, terraces and the like and may be the surface of a layer of material different from that of the rest of the substrate.

While the particular embodiment of the present invention has been shown and described, it will be obvious to those skilled in the art that changes and modifications may be made without departing from the teachings of the invention.

The matter set forth in the foregoing description and accompanying drawings is offered by way of illustration only and not as a limitation. The actual scope of the invention is intended to be defined in the following claims when viewed in their proper perspective based on the prior art.

I claim:

1. A method for controlling a biosensor system to determine interaction kinetics for an analyte, the method comprising:
    a) monitoring binding of said analyte, said analyte contained in a solution, to an immobilized ligand or analogue thereof, the immobilized ligand or analogue thereof immobilized on an optical sensor surface, wherein the binding is measured as a resulting change in a property of said surface indicative of at least a dissociation phase between the ligand or analogue and the analyte;
    b) automatically determining said interaction kinetics, wherein determining further includes:
        defining a first part of the dissociation phase that includes kinetic information;
        excluding a second part of the dissociation phase as including non-kinetic information; and
        fitting an interaction model to the first part of the dissociation phase to automatically determine said interaction kinetics with respect to the ligand and the analyte; and
    c) triggering control software to stop data generation when the dissociation phase is complete.

2. The method according to claim 1, wherein said ligand, or analogue thereto, is immobilized to a series of surfaces.

3. The method according to claim 1, wherein said optical sensor surface is part of a detector based upon evanescent wave sensing.

4. The method according to claim 3, wherein said evanescent wave sensing is based on surface plasmon resonance.

5. The method according to claim 1, wherein defining parts of the dissociation phase that contains kinetic information for fitting is done by excluding response data less than:

$$R = Y_{high}/x,$$

wherein R is the response in RU below which dissociation phase data is excluded from fitting,
$Y_{high}$ is the highest response relative to baseline during the dissociation phase on each curve, and
x is an arbitrary number set by user or coded in program software.

6. The method according to claim 5, wherein x is 20.

7. The method according to claim 1, wherein defining parts of the dissociation phase that contains kinetic information for fitting is done by excluding response data less than R=0 (baseline), wherein R is the response in RU below which dissociation phase data is excluded from fitting.

8. The method according to claim 1, wherein defining parts of the dissociation phase that contains kinetic information for fitting is done by excluding response data less than R=x (x is a number set by user or coded in a program), wherein R is the response in RU below which dissociation phase data is excluded from fitting.

9. The method according to claim 1, wherein said determining further includes adjusting dissociation phase data for drifts, disturbances or single deviating curves for fitting.

10. An analytical system for studying molecular interactions, which system comprises computer processing means including program code means for performing a method for controlling a biosensor system to determine interaction kinetics for an analyte, the method including:
    monitoring binding of an analyte in a solution with an immobilized ligand or analogue on an optical sensor surface, wherein the binding is measured as a resulting change in a property of said surface indicative of at least a dissociation phase between the ligand or analogue and the analyte; and
    automatically determining said interaction kinetics, wherein determining further includes:
        defining a first part of the dissociation phase that includes kinetic information;
        excluding a second part of the dissociation phase as including non-kinetic information;
        fitting an interaction model to the first part of the dissociation phase to determine said interaction kinetics with respect to the ligand and the analyte; and
    triggering control software to stop data generation when the dissociation phase is complete.

11. A computer program product comprising program code means stored on a computer readable medium to implement a method for controlling a biosensor system to determine interaction kinetics for an analyte, the method including:
    monitoring binding of an analyte in a solution with an immobilized ligand or analogue on an optical sensor surface, wherein the binding is measured as a resulting change in a property of said surface indicative of at least a dissociation phase between the ligand or analogue and the analyte; and
    automatically determining said interaction kinetics, wherein determining further includes:
        defining a first part of the dissociation phase that includes kinetic information;
        excluding a second part of the dissociation phase as including non-kinetic information;
        fitting an interaction model to the first part of the dissociation phase to determine said interaction kinetics with respect to the ligand and the analyte; and
    triggering control software to stop data generation when the dissociation phase is complete.

* * * * *